US008585636B2

(12) United States Patent
Staggs et al.

(10) Patent No.: US 8,585,636 B2
(45) Date of Patent: Nov. 19, 2013

(54) MEDICAL DEVICE RECEPTACLE FILLING METHOD AND APPARATUS

(75) Inventors: James W. Staggs, Laguna Niguel, CA (US); Catherine P. Ha, Westminster, CA (US); Wayne S. Wong, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/299,610

(22) Filed: Nov. 18, 2011

(65) Prior Publication Data

US 2013/0131611 A1 May 23, 2013

(51) Int. Cl.
*A61M 1/00* (2006.01)
(52) U.S. Cl.
USPC .......................................... 604/30
(58) Field of Classification Search
USPC ............................ 604/22, 30, 506
See application file for complete search history.

(56) References Cited

U.S. PATENT DOCUMENTS

| 7,753,880 B2 * | 7/2010 | Malackowski | 604/131 |
| 2006/0073048 A1 * | 4/2006 | Malackowski | 417/474 |
| 2007/0135752 A1 * | 6/2007 | Domash et al. | 604/19 |
| 2008/0110236 A1 | 5/2008 | Hajishah et al. | |
| 2008/0312953 A1 | 12/2008 | Claus | |
| 2009/0182266 A1 | 7/2009 | Gordon et al. | |
| 2010/0121257 A1 * | 5/2010 | King | 604/22 |
| 2010/0228222 A1 | 9/2010 | Williams et al. | |

FOREIGN PATENT DOCUMENTS

EP 2014266 A1 1/2009

OTHER PUBLICATIONS

International Search Report and Written Opinion for Application No. PCT/US2012/065482, mailed on Feb. 13, 2013, 12 pages.

* cited by examiner

*Primary Examiner* — Aarti B Berdichevsky
(74) *Attorney, Agent, or Firm* — Abbott Medical Optics Inc.

(57) ABSTRACT

An apparatus and method for dispersing fluid from a fluid dispersal line is provided. The method comprises initiating operation of the medical apparatus, determining whether fluid has been dispersed from the medical apparatus via the fluid dispersal line since said initiating occurred, and assessing whether fluid is available in the fluid dispersal line. If fluid has not been dispersed from the medical apparatus since said initiating occurred and fluid is not available in the fluid dispersal line, the method includes distributing a commanded quantity of fluid plus an amount of fluid determined to fill the fluid dispersal line. Otherwise the method disperses only the commanded quantity of fluid.

20 Claims, 6 Drawing Sheets

MEDICAL DEVICE RECEPTACLE FILLING METHOD AND APPARATUS

BACKGROUND

1. Field

The present invention relates generally to fluid management in association with a medical device, and more specifically to filling a cup or other receptacle using a device such as a phacoemulsification machine in an efficient manner.

2. Background

Surgical systems, such as phacoemulsification systems for ophthalmic surgery, require fluid infusion while the surgery is being performed. Such systems typically employ machines that perform a host of relevant functions, both with respect to electrical or ultrasonic operation and fluid operation.

Fluid flow is typically controlled during an ophthalmic or ocular surgical procedure by the phacoemulsification machine adjusting the height of an infusion bottle or other irrigation fluid source. Fluid flows from the irrigation source to the phacoemulsification machine and to the ocular region of the patient using a series of tubes or lines. One attribute of currently available devices such as phacoemulsification machines is the ability to deliver fluid via an alternate fluid path, called the "cup fill" feature or mode. Operating room personnel sometimes wish to obtain BSS (balanced salt solution) before a surgical procedure, but unhooking a bottle or other irrigation fluid source is time consuming and potentially both wasteful and unsanitary.

Operating room personnel frequently want BSS available in cups or other receptacles for manual use with the patient. Offering a "cup fill" feature or mode is therefore desirable. Operating room personnel use the cup fill feature and subsequently employ a syringe to dispense fluid from the cup onto the patient's eye, with the intent of keeping the eye hydrated so that it is easier for the surgeon to see particles and ocular features. Cups or receptacles of fluid may also be employed to perform hydrodissection within the eye, and at the end of the procedure such fluid may be used to hydrate the stroma at the incision, resulting in the tissue expanding and a better incision seal.

Certain phacoemulsification machines offer a cup fill feature via user selection using a graphical user interface. Selectable amounts of fluid are offered, such as three selectable amounts. Some systems require priming of the lines, but certain users prime lines in certain situations, while other users do not prime the fluid lines in the same situations. As a result, nonstandard amounts of fluid can be distributed via the fluid lines when the cup fill feature is selected, and as a result differing amounts of fluid may be dispersed to the user's receptacle in spite of the fact that the user has selected a uniform or known amount of fluid. This is problematic in that excessive amounts of fluid sent to the receptacle can cause overflow of the receptacle, resulting in fluid spills. Alternately, but with similar spill results, selecting the cup fill feature with a request for a standard amount of fluid may result in a smaller amount of fluid being provided than was requested. In this situation, the user may again initiate a cup fill command, resulting in overflow of the receptacle.

There is therefore a need in the art for techniques and devices that can provide efficient and effective receptacle filling performance in connection with a device such as a phacoemulsification machine that reduces potential for spillage or overflow when filling such receptacles.

SUMMARY

An apparatus and method for dispersing fluid from a fluid dispersal line is provided. The method comprises initiating operation of the medical apparatus, determining whether fluid has been dispersed from the medical apparatus via the fluid dispersal line since said initiating occurred, and assessing whether fluid is available in the fluid dispersal line. If fluid has not been dispersed from the medical apparatus since said initiating occurred and fluid is not available in the fluid dispersal line, the method includes distributing a commanded quantity of fluid plus an amount of fluid determined to fill the fluid dispersal line. Otherwise the method includes dispersing only the commanded quantity of fluid.

Other features and advantages of the present invention should be apparent from the following description of exemplary embodiments, which illustrate, by way of example, aspects of the invention.

DETAILED DESCRIPTION

One aspect of the present invention is the ability for a device such as a phacoemulsification machine to assess the fill quantity of a cup fill or fluid dispersal line, such as by either determining that the machine, or more specifically, the line, contains fluid, or that the cup fill function has previously been employed, indicating a primed condition. If the machine/line has not been primed, the system determines an amount of fluid to prime the line and delivers the requested amount of fluid and enough fluid to prime the line. If the machine/line has been primed, the machine simply delivers the requested amount of fluid.

Figure 1:
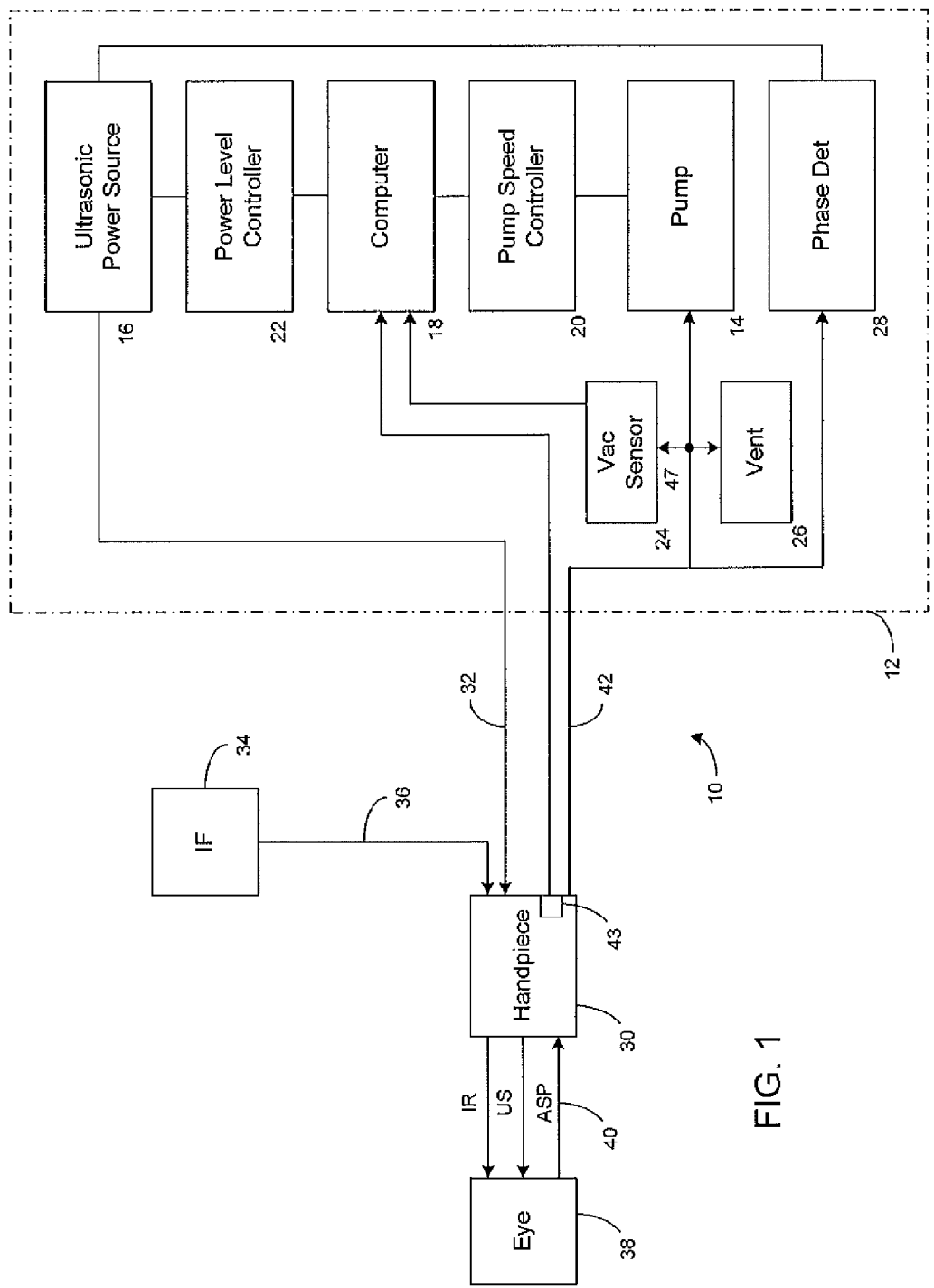
FIG. 1 illustrates a typical phacoemulsification system.

FIG. 1 illustrates a typical phacoemulsification system 10. The system includes a control unit 12, indicated by the dashed lines in FIG. 1 which includes a pump 14, which provides a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the input side of pump 14. Suitable venting is provided by vent 26. Examples of pump 14 include a peristaltic pump and a Venturi pump, but other types of pumps or combination of pumps may be employed.

Phase detector 28 provides an input to computer 18 representing a phase shift between a sine wave representation of the voltage applied to a handpiece 30 and the resultant current into the handpiece 30. The block representation of the handpiece 30 includes a needle and electrical means, typically a piezoelectric crystal, for ultrasonically vibrating the needle. Control unit 12 supplies power on line 32 to a phacoemulsification handpiece 30. An irrigation fluid source 34 is fluidly coupled to handpiece 30 through line 36. The irrigation fluid and ultrasonic power are applied by handpiece 30 to a patient's eye, or affected area or region, indicated diagrammatically by block 38, and may include a lumen (not shown). Alternatively, the irrigation source may be routed to eye 38 through a separate pathway independent of the handpiece.

Eye 38 is aspirated by the control unit peristaltic pump 14 through line/handpiece needle 40 and line 42. A switch 43 disposed on the handpiece 30 may be utilized as a means for enabling a surgeon/operator to select an amplitude of electrical pulses to the handpiece via the computer 18, power level controller 22 and ultrasonic power source 16 as discussed herein. Any suitable input means, such as, for example, a foot pedal (not shown) may be utilized in lieu of the switch 43.

Figure 2:
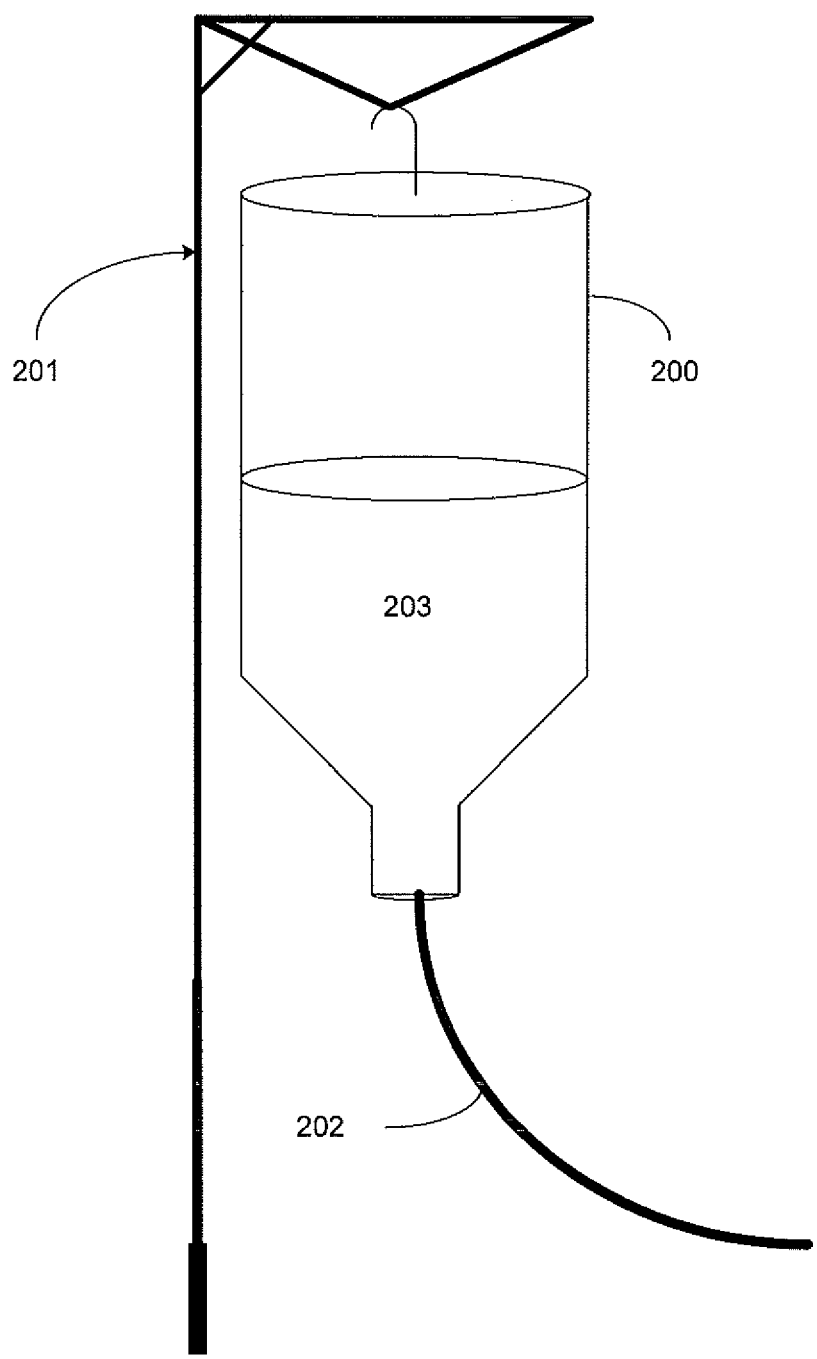
FIG. 2 is one example of an irrigation fluid source in the form of a BSS (balanced salt solution) bottle.

The term "irrigation fluid source" is used throughout this discussion and is intended to be interpreted a broadly as possible to include virtually anything that can deliver fluid to a patient, or more particularly, a patient's eye. In one embodiment, the irrigation fluid source may be any fluid source conveying fluid through the phacoemulsification system 10 to the patient. In its most common form, irrigation fluid source 34 typically takes the form of a gravity fed device such as an infusion bottle 200 containing fluid 203, an example of which is shown in FIG. 2. Other irrigation fluid sources may be employed, such as a collapsible bag or other fluid maintaining device. The irrigation fluid source typically is placed on a device such as the retractable metal tube or tube arrangement 201 shown in FIG. 2 and controllable by control unit 12. In essence, control unit 12 commands the retractable metal tube or tube arrangement to extend or retract, thereby raising or lowering the irrigation fluid source and altering fluid flow through a line or tube such as line 202 in FIG. 2. Height of the retractable metal tube or tube arrangement 201, or amount of flow from infusion bottle 200 via tube 202, is controlled using control unit 12.

Figure 3:
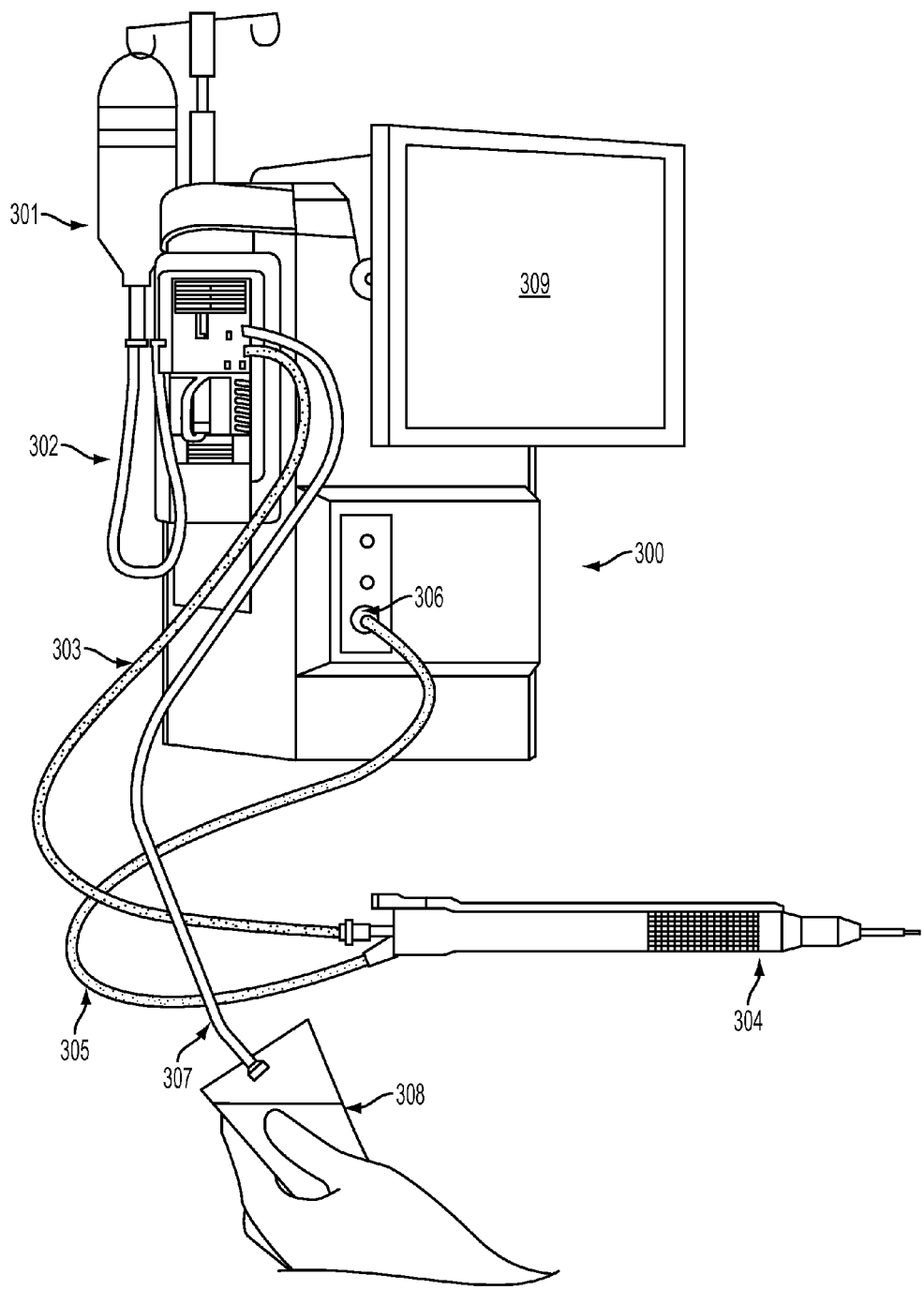
FIG. 3 shows an embodiment of the present design with the fluid dispersal line in an "unprimed" state.

FIG. 3 illustrates one general embodiment of the present design, and in particular the present design in an "unprimed" or "not primed" state. Irrigation fluid source 301 passes fluid via line or tube 302 to phacoemulsification machine 300. While shown in this view with a phacoemulsification machine, it is to be understood that the present design may be employed with any type of device that distributes liquid and may need to be primed. "Primed" in this context means that fluid lines are completely or partially filled with liquid. Such a design as shown in FIG. 3 may offer the functional capability to control the liquid amount distributed. A fluid line or fluid lines in the present design may take any form, including intermediate fluid holding or conveyance devices.

In the device shown in FIG. 3, fluid may be provided to phacoemulsification machine 300 via line or tube 302. Fluid may be pumped or otherwise distributed, possibly through certain devices (not shown) inside or associated with phacoemulsification machine 300, such as fluid cassettes, via peristaltic or vacuum or other pumps or combination of pumps, through fluid dispersal line 307. FIG. 3 shows fluid dispersal line 307 dispersing fluid to receptacle 308. During the surgical procedure, fluid dispersal line is connected to handpiece 304 via the top port shown in FIG. 3. The handpiece 304 shown also collects fluid from the ocular region of the patient and returns the fluid via line 303. Power line 305 provides power to the handpiece and is connected to phacoemulsification machine 300 at point 306. Not shown in this view are the collection fluidics, which may include collection bags or devices, filtering devices, disposal fluidics, and so forth.

Fluid output from phacoemulsification machine 300 may therefore be provided via cup fill or fluid dispersal line 307. While shown as a separate line in this configuration, it is to be understood that any form of liquid distribution mechanism may be employed (nozzle, simple port opening, or otherwise). As an alternate to a single cup fill line, fluid from the phacoemulsification machine 300 to the handpiece 304 or any similar device may be diverted to a separate cup fill line or port in phacoemulsification machine 300 such that a single line comes from the phacoemulsification machine 300 and splits into two lines, a cup fill or fluid dispersal line and a handpiece line. This implementation results in a single line and fluid output port being used for both fluid operation during a medical procedure and cup fill function. In some arrangements, such as the arrangement of FIG. 3, the cup fill line may be the handpiece fill line, where the cup fill line is temporarily disconnected from the handpiece or other device. In short, any type of fluidics, including but not limited to openings, combinations of lines, and so forth may be used in order to fill receptacle 308, where in FIG. 3 the receptacle 308 shown is a cup.

Figure 4:
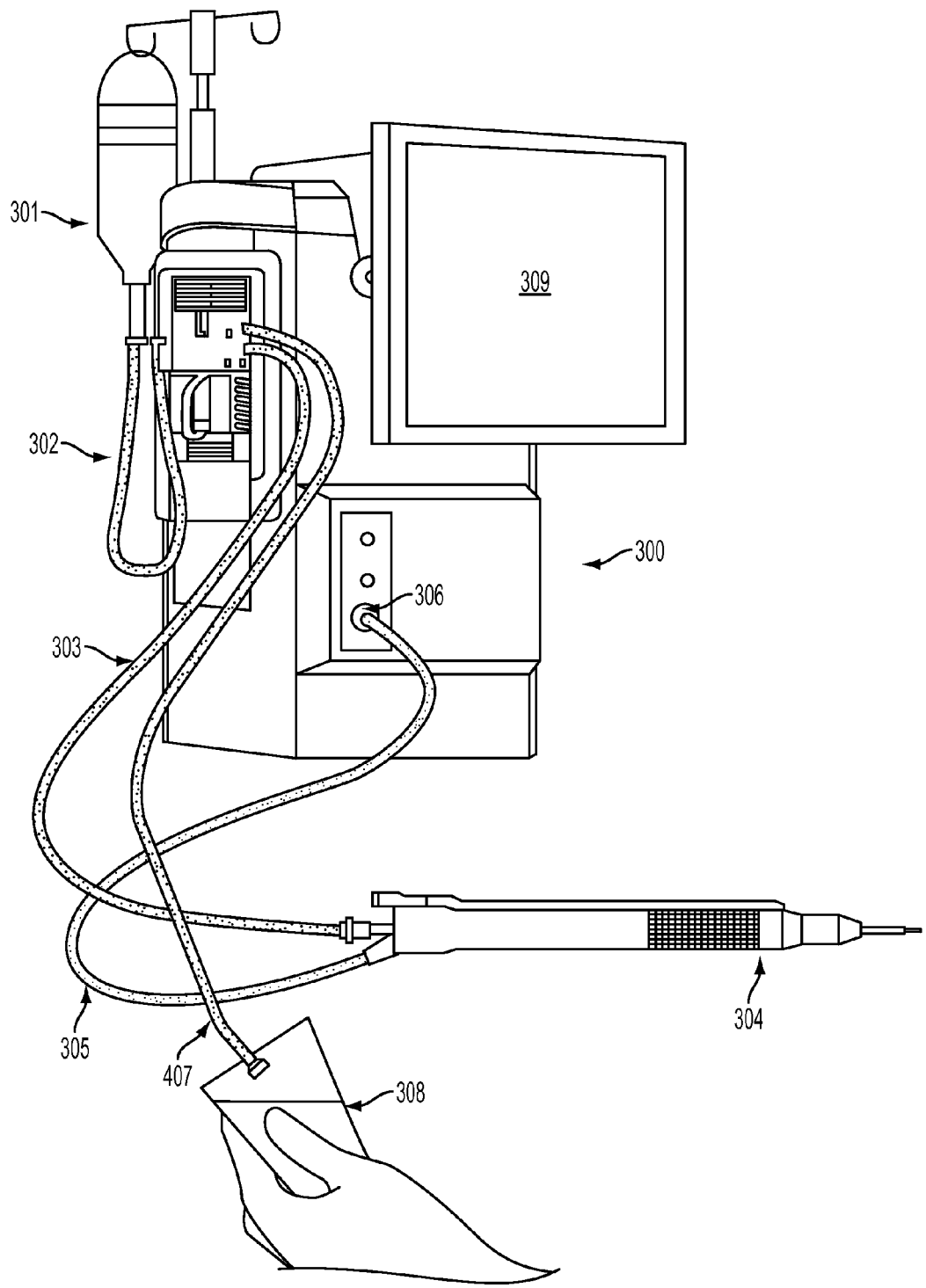
FIG. 4 illustrates an embodiment of the present design with the fluid dispersal line in a "primed" state.

In the depiction of FIG. 3, the cup fill line or fluid dispersal line 307 is shown to be empty or unprinted. The user may be offered an ability to request distribution of fluid from phacoemulsification machine 300 using a graphical user interface 309. The graphical user interface 309 may provide information and data to other components in phacoemulsification machine 300 to carry out desired functionality. Multiple cup fill levels may be offered, and the user may select one fill level for use and distribution of liquids to a desired receptacle. For example, the user may be offered three cup fill levels, P, Q, and R fluid ounces. Other measures may be employed and/or offered. Different functionality may be provided by the graphical user interface 309 based on desired cup fill operation, such as offering a single cup fill value, offering a numerical setting for number of ounces to be distributed, a simple on/off switch for fluid distribution, and so forth. Such a graphical user interface 309 may allow user entry of information via a series of buttons, a keyboard and/or mouse, or any other user interface device known in the art. FIG. 4 illustrates the same design as presented in FIG. 3 with cup fill line 407 being primed or filled with fluid.

As noted, the issue with filling cups or receptacles in such an arrangement is that the user may be uncertain whether the lines and/or machine have been primed fully, primed partially, or are unprimed. In such a circumstance, the user may believe the system has been primed when it has not, may request distribution of X fluid ounces of BSS, and may only receive some percentage of X in her receptacle. The user may then request an additional amount of fluid be distributed, at which time the receptacle may be overfilled and may spill. The converse is the user's belief that the system has not been primed when in fact it has, and requesting X fluid ounces of BSS results in a distribution of greater than X ounces of fluid, most likely spilling out of the receptacle.

Figure 5:
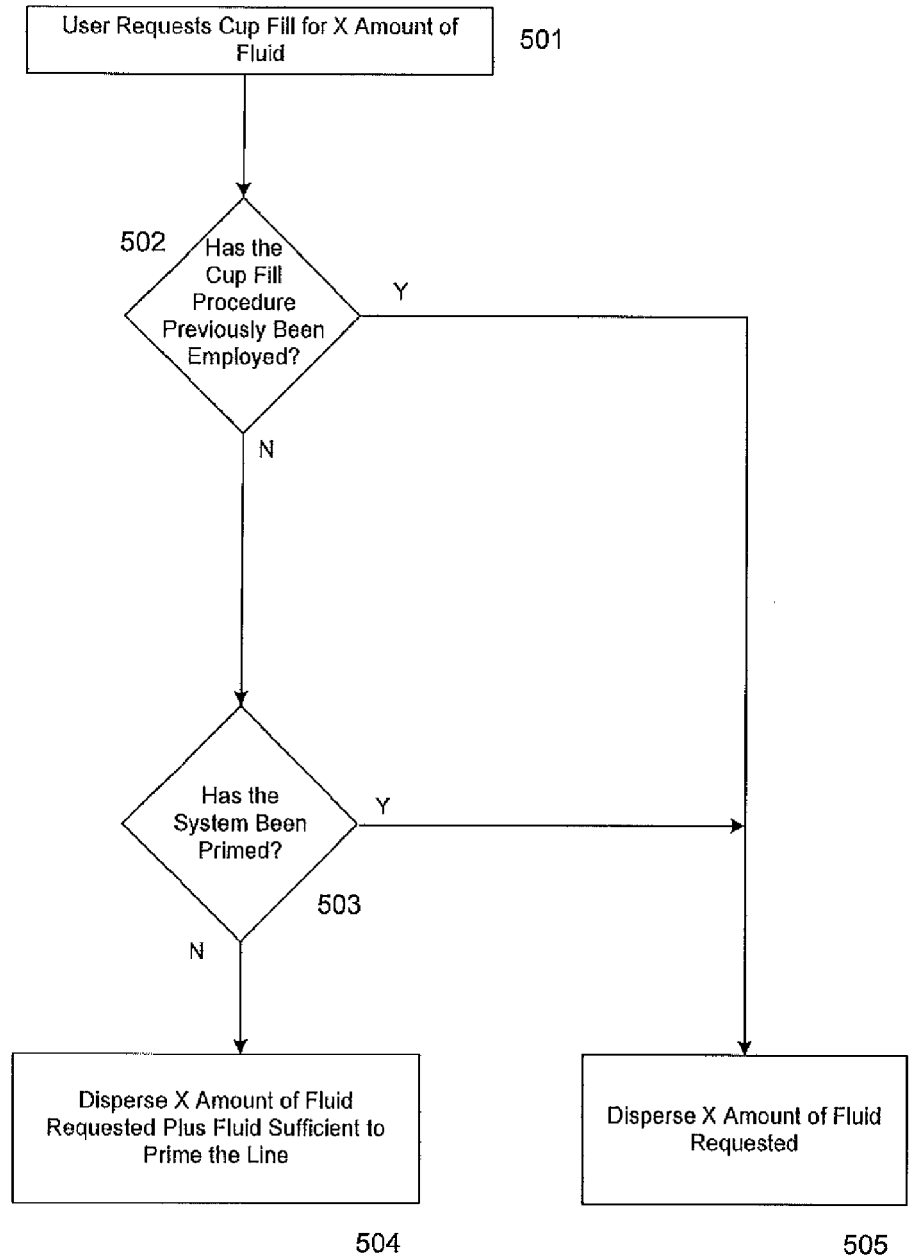
FIG. 5 shows a flowchart of operation of one embodiment of the present design.

The present design addresses this problem by evaluating the status of the cup fill line or lines, or otherwise evaluating the primed status of the machine, and distributing only the requested amount of fluid. FIG. 5 illustrates a general flowchart for one embodiment of the present design. At point 501, the user requests a cup fill for X ounces of fluid. The system may determine, at point 502, whether the cup fill function had been previously employed.

With respect to the evaluation at point 502, it should be noted that a typical phacoemulsification machine is initially powered on, fluid made available from an irrigation fluid source, and a cup fill procedure may be requested. If the machine has been turned on but the line not filled or primed, the line is empty, no fluid is present in the line, including the cup fill line. If a cup fill procedure has occurred since the machine was powered up or turned on, the cup fill fluid line contains fluid and as a result remains primed until such time as the machine is turned off. Once the machine is turned off, or in some instances once the surgical procedure is finished, the machine and lines are typically flushed of fluid. Thus it is assumed that once the system is primed, it remains primed for the remainder of the time in operation. In other instances, such as a periodic flush of lines including the cup fill line, or if another arrangement differing from those depicted in FIGS. 3 and 4 is employed, the system will need to monitor fluid level in the line(s) in some manner to perform the functionality claimed herein.

Thus with respect to the evaluation at point 502, the system may determine whether a cup fill procedure has previously occurred. In normal operation, this indicates that the cup fill line is primed. If not, operation progresses to point 503. If the system periodically flushes the cup fill line, or enables the user to flush the cup fill line, or some other occurrence partially or completely empties the cup fill line, point 502 may evaluate simply whether fluid exists in the cup fill line by some other fluid line content monitoring functionality.

Point 503 evaluates whether the system has been primed, such as by evaluating a priming indication. Priming indication in this instance may be provided manually by the user or some other individual, such as via the graphical user interface. Alternately, the device may make an assessment as to whether the device has been primed or not. Evaluation at point 503 may instead include an assessment of the amount of fluid actually or believed to be present in the line. In one aspect, the device may monitor the amount of fluid that passes to the cup fill line. In another aspect, the system may have a sensor that monitors the cup fill line, such as optically, or monitors the distribution of fluid from the cup fill line. Some type of floating member may be employed in the line that can be monitored from outside the line, with appropriate filtering to ensure the floating member will not be expelled from the monitored region of the line. Other priming assessment mechanisms known in the art may be employed, with the general goal being to assess the amount of fluid actually present or believed to be present in the fill line.

If fluid has been provided previously, or the system is primed, point 504 disperses fluid equal to the amount of fluid requested. For example, if X fluid ounces are requested, the system provides X fluid ounces through the primed or previously employed line or lines. If, however, the system is neither primed nor any fluid provided previously, the system at point 505 provides fluid sufficient to both fill the line and provide the fluid requested by the user. If X fluid ounces are requested by the user, and the empty, unprimed lines hold a known quantity of fluid, such as Y fluid ounces, the system seeks to provide X plus Y fluid ounces, priming the lines and providing the requested X fluid ounces. In this manner, the requested amount of fluid is always the amount of fluid provided.

In a case where the lines are periodically flushed, or it is unknown at any given time whether fluid exists in the line, the system seeks to assess whether the line is full or empty or at some level in between at the time fluid is requested via a cup fill procedure. Such operation again requires some ability to assess the fluid in the cup fill line, but an alternative is to simply prime the line in all cases, or require line priming as a prerequisite to obtaining fluid via the cup fill procedure. While such a requirement may expel fluid unnecessarily, it may be less costly than providing line monitoring equipment, such as line monitoring sensors, to monitor fluid level and assess line fill conditions.

The amount of fluid in the line may be an inexact determination, in that a de minimis or minor amount of fluid may be available, or some intermediate percentage filled, such as $1/3$, $1/2$, or $3/4$ full. In the situation where the line is neither completely empty nor completely full, the system may determine that amount of fluid in the line is less than 100 percent and may provide X fluid ounces, not accounting for the fluid needed to completely prime the line. In other instances, the system may determine that an amount of fluid is present in the line below a certain threshold and may therefore attempt to prime the line and fill the receptacle. In another embodiment, a sensor may be employed to assess the exact amount of fluid in the line. For example, if the line holds Y ounces of fluid and the system senses F fluid ounces in the line, the system may disperse the commanded X plus (Y minus F) fluid ounces in an attempt to completely prime the line. In summary, implementation may vary for an intermediate line fill condition depending on the desire of the designer.

Further, one alternative to the design of FIG. 5 is to simply prime the system when a cup fill procedure is first requested. This may again result in expulsion of excess amounts of fluid, but may be simpler and less expensive and thus preferred in certain instances.

Figure 6:
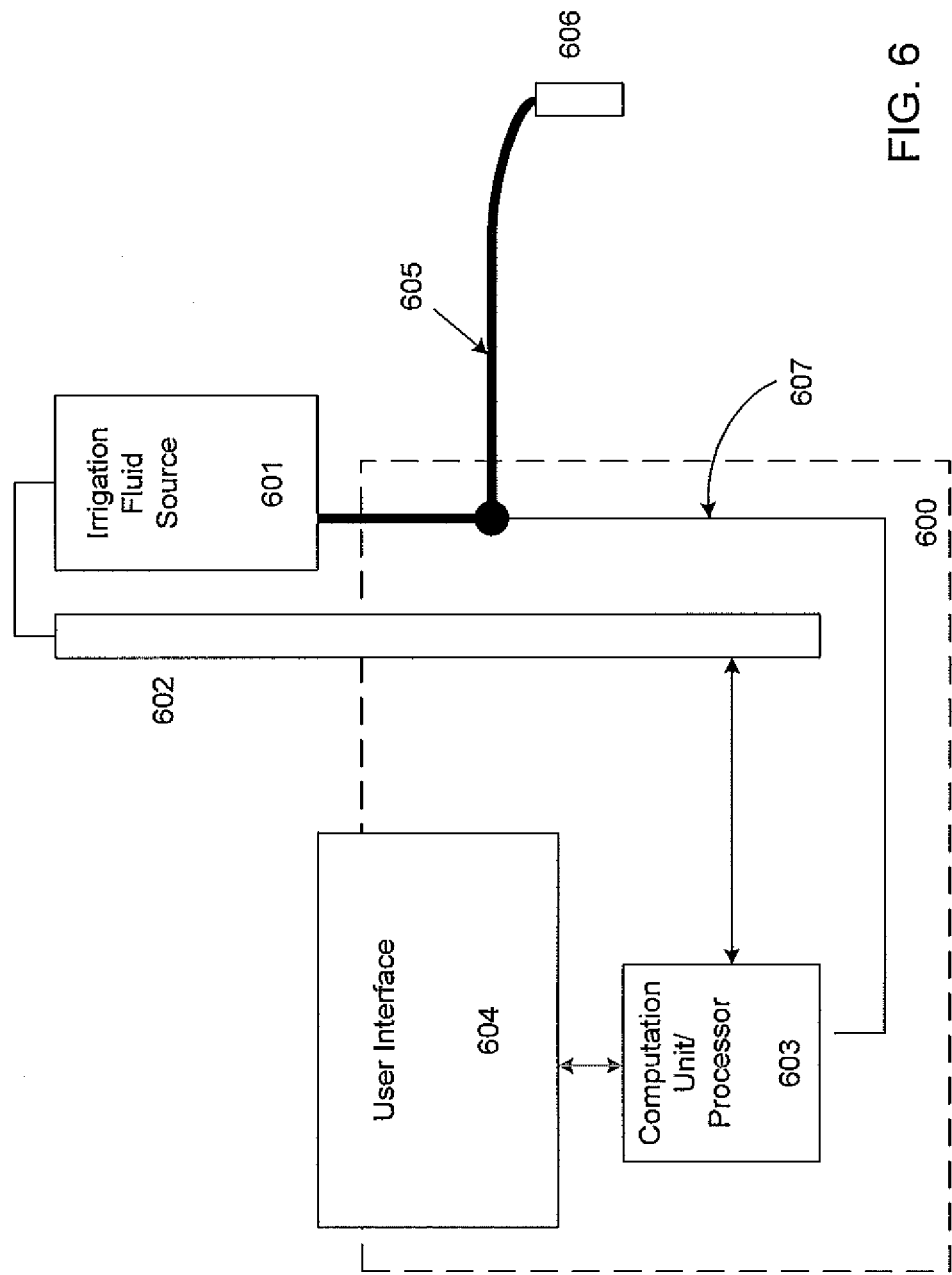
FIG. 6 is a basic schematic of the components of one embodiment of the present design.

FIG. 6 illustrates a schematic of the basic components of the present design. From FIG. 6, there is shown an irrigation fluid source 601 suspended at a first height using a retractable tubular arrangement 602. A processor or computation unit 603 is typically located inside phacoemulsification device 600. The processor or computation unit 603 may receive indications from the user via user interface 604. The processor or computation unit 603 may make the determinations necessary to disperse the appropriate amount of fluid, such as determining the primed state or whether the user has indicated he primed the system. The processor or computation unit 603 may make such a determination and provide the requested amount of fluid by commanding such fluid to be transmitted through line or tube 605 via phacoemulsification device 600 to receptacle 606. Note that in FIG. 6 the fluid line or cup fill line is shown passing through phacoemulsification device 600. Such a path is consistent with the illustrations in FIGS. 3 and 4. Line 607 represents a connection between the computation unit 604 and the line or tube 605 within the phacoemulsification device 600. While illustrated as connecting the computation unit 604 and the line or tube 605, the computation unit may connect to any suitable component, including but not limited to the irrigation fluid source 601, to command dispersal of the desired amount of fluid. The goal is dispersal of an appropriate amount of fluid to the receptacle 606. The design may further include a sensor (not shown) proximate the line or tube 605 or irrigation fluid source 601 to monitor amount of fluid distributed if desired. Programming of such operation of the present design may be done by one skilled in the art and is fairly straightforward.

Those of skill in the art will recognize that the step of a method described in connection with an embodiment may be interchanged without departing from the scope of the invention. Those of skill in the art would also understand that information and signals may be represented using any of a variety of different technologies and techniques. For example, data, data packets, packet groups, instructions, commands, information, signals, and bits that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for dispersing fluid from a fluid dispersal line connected to a medical apparatus, the method comprising:
    initiating operation of the medical apparatus;
    determining whether fluid has been dispersed from the medical apparatus via the fluid dispersal line since said initiating occurred; and
    assessing whether fluid is available in the fluid dispersal line;
    wherein if fluid has not been dispersed from the medical apparatus since said initiating occurred and fluid is not available in the fluid dispersal line, distributing a commanded quantity of fluid plus an amount of fluid determined to fill the fluid dispersal line, and otherwise dispersing only the commanded quantity of fluid.

2. The method of claim 1, wherein assessing whether fluid is available in the fluid dispersal line comprises assessing whether a user indication that the fluid dispersal line has been primed has been provided, wherein primed comprises filled with fluid.

3. The method of claim 1, wherein assessing whether fluid is available in the fluid dispersal line comprises employing a sensing device to sense the amount of fluid present in the fluid dispersal line.

4. The method of claim 1, wherein said fluid dispersal line comprises a fluid line primarily provided within the medical apparatus.

5. The method of claim 1, wherein the fluid dispersal line is configured to connect to a handpiece.

6. The method of claim 1, wherein the medical apparatus comprises a phacoemulsification machine configured to perform the method when indicated by a user via a graphical user interface.

7. A medical apparatus configured to disperse a commanded quantity of fluid, comprising:
    a fluid source;
    a fluid dispersal line; and
    a processor configured to determine whether fluid has been dispersed from the medical apparatus via the fluid dispersal line since the medical apparatus initiated operation, and assess whether fluid is available in the fluid dispersal line;
    wherein if fluid has not been dispersed from the medical apparatus since the medical apparatus initiated operation and fluid is not available in the fluid dispersal line, distributing the commanded quantity of fluid plus an amount of fluid determined to fill the fluid dispersal line, and otherwise dispersing only the commanded quantity of fluid.

8. The medical apparatus of claim 7, wherein the processor being configured to assess whether fluid is available in the fluid dispersal line comprises the processor being configured to assess whether a user indication that the fluid dispersal line has been primed has been provided, wherein primed comprises filled with fluid.

9. The medical apparatus of claim 7, wherein the processor being configured to assess whether fluid is available in the fluid dispersal line comprises the processor being configured to sense the amount of fluid present in the fluid dispersal line using a sensing device.

10. The medical apparatus of claim 7, wherein the fluid dispersal line comprises a fluid line primarily provided within the medical apparatus.

11. The medical apparatus of claim 7, wherein the fluid dispersal line comprises a series of fluid maintenance devices.

12. The medical apparatus of claim 7, wherein the fluid dispersal line is configured to connect to a handpiece.

13. The medical apparatus of claim 7, wherein the medical apparatus comprises a phacoemulsification machine having a graphical user interface.

14. A method for dispersing fluid from a fluid dispersal line connected to a medical apparatus, the method comprising:
    initiating operation of the medical apparatus;
    determining whether fluid has been dispersed from the medical apparatus via the fluid dispersal line since said initiating occurred; and
    assessing whether fluid is available in the fluid dispersal line;
    wherein if fluid has not been dispersed from the medical apparatus since said initiating occurred and fluid is not available in the fluid dispersal line, distributing a commanded quantity of fluid plus an amount of fluid determined to fill the fluid dispersal line.

15. The method of claim 14, wherein if fluid has been dispersed from the medical apparatus since said initiating occurred or fluid is available in the fluid dispersal line, dispersing only the commanded quantity of fluid.

16. The method of claim 14, wherein assessing whether fluid is available in the fluid dispersal line comprises assessing whether a user indication that the fluid dispersal line has been primed has been provided, wherein primed comprises filled with fluid.

17. The method of claim 14, wherein assessing whether fluid is available in the fluid dispersal line comprises employing a sensing device to sense the amount of fluid present in the fluid dispersal line.

18. The method of claim 14, wherein said fluid dispersal line comprises a fluid line primarily provided within the medical apparatus.

19. The method of claim 14, wherein the fluid dispersal line is configured to connect to a handpiece.

20. The method of claim 14, wherein the medical apparatus comprises a phacoemulsification machine configured to perform the method when indicated by a user via a graphical user interface.

\* \* \* \* \*